(12) United States Patent
Yeatman et al.

(10) Patent No.: US 8,642,349 B1
(45) Date of Patent: Feb. 4, 2014

(54) ARTIFICIAL NEURAL NETWORK PROTEOMIC TUMOR CLASSIFICATION

(75) Inventors: Timothy J. Yeatman, Thonotosassa, FL (US); Jeff Xiwu Zhou, Potomac, MD (US); Gregory C. Bloom, Tampa, FL (US); Steven A. Eschrich, Lakeland, FL (US)

(73) Assignees: H. Lee Moffitt Cancer Center and Research Institute, Inc., Tampa, FL (US); University of South Florida, Tampa, FL (US)

( * ) Notice: Subject to any disclaimer, the term of this patent is extended or adjusted under 35 U.S.C. 154(b) by 1418 days.

(21) Appl. No.: 11/837,883

(22) Filed: Aug. 13, 2007

Related U.S. Application Data

(60) Provisional application No. 60/822,148, filed on Aug. 11, 2006.

(51) Int. Cl.
 *G01N 33/00* (2006.01)
(52) U.S. Cl.
 USPC .......................................................... 436/86
(58) Field of Classification Search
 USPC ........................................................... 436/86
 See application file for complete search history.

(56) References Cited

U.S. PATENT DOCUMENTS

2005/0048564 A1 3/2005 Emili et al.
2007/0111257 A1 5/2007 Kohne

OTHER PUBLICATIONS

Buckhaults et al. "Identifying tumor origin using a gene expression-based classification map", Cancer Research, 2003, 63:4144-4149.*
Hirano et al. "Relationship between TA01 and TA02 polypeptides associated with lung adenocarcinoma and histocytological features", British Journal of Cancer, 1997, 75(7):978-985.*
Hirano et al. "Usefulness of TA02 (napsin A) to distinguish primary lung adenocarcinoma from metastatic lung adenocarcinoma", Lung Cancer, 2003, 41:155-162.*
Hellman et al. "Protein expression patterns in primary carcinoma of the vagina", British Journal of Cancer, 2004, 91:319-326.*
He et al. "Diverse proteomic alterations in gastric adenocarcinoma", Proteomics, 2004, 4:3276-3287.*
Blaszyk H., Hartmann A., Bjornsson J. Cancer of unknown primary: clinicopathologic correlations. Apmis 2003;111:1089-94.
Hainsworth JD, and Greco FA. Treatment of patients with cancer of an unknown primary site. N Engl J Med 1993;329: 257-63.
Shipp MA, Ross KN, Tamayo P, Weng AP, Kutok JL, Aguiar RC, Gaasenbeek M, Angelo M, Reich M, Pinkus GS, Ray TS, and Koval MA, et al. Diffuse large B-cell lymphoma outcome prediction by gene-expression profiling and supervised machine learning. Nat Med 2002;8: 68-74.
Sorlie T, Perou CM, Tibshirani R, Aas T, Geisler S, Johnsen H, Hastie T, Eisen MB, Van De Rijn M, Jeffrey SS, Thorsen T, and Quist H, et al. Gene expression patterns of breast carcinomas distinguish tumor subclasses with clinical implications. Proc Natl Acad Sci U S A 2001;98: 10869-74.
Alizadeh AA, Eisen MB, Davis RE, Ma C, Lossos IS, Rosenwald A, Boldrick JC, Sabet H, Tran T, Yu X, Powell JI, and Yang L, et al. Distinct types of diffuse large B-cell lymphoma identified by gene expression profiling. Nature 2000;403: 503-11.
Rosenwald A, Wright G, Chan WC, Connors JM, Campo E, Fisher RI, Gascoyne RD, Mullerhermelink HK, Smeland EB, Giltnane JM, Hurt EM, and Zhao H, et al. The use of molecular profiling to predict survival after chemotherapy for diffuse large-B-cell lymphoma. N Engl J Med 2002;346: 1937-47.
Van'T Veer LJ, Dai H, Van De Vijver MJ, He YD, Hart AA, Mao M, Peterse HL, Van Der Kooy K, Marton MJ, Witteveen AT, Schreiber GJ, and Kerkhoven RM, et al. Gene expression profiling predicts clinical outcome of breast cancer. Nature 2002;415: 530-6.
Van De Vijver MJ, He YD, Van'T Veer LJ, Dai H, Hart AA, Voskuil DW, Schreiber GJ, Peterse JL, Roberts C, Marton MJ, Parrish M, and Atsna D, et al. A gene-expression signature as a predictor of survival in breast cancer. N Engl J Med 2002;347: 1999-2009.
Takahashi M, Rhodes DR, Furge KA, Kanayama H, Kagawa S, Haab BB, and Teh BT. Gene expression profiling of clear cell renal cell carcinoma: gene identification and prognostic classification. Proc Natl Acad Sci U S A 2001;98: 9754-9.
Pomeroy SL, Tamayo P, Gaasenbeek M, Sturla LM, Angelo M, McLaughlin ME, Kim JY, Goumnerova LC, Black PM, Lau C, Allen JC, and Zagzag D, et al. Prediction of central nervous system embryonal tumour outcome based on gene expression. Nature 2002;415: 436-42.
Beer DG, Kardia SL, Huang CC, Giordano TJ, Levin AM, Misek DE, Lin L, Chen G, Gharib TG, Thomas DG, Lizyness ML, and Kuick R, et al. Gene-expression profiles predict survival of patients with lung adenocarcinoma. Nat Med 2002;8: 816-24.
Dyrskjot L, Thykjaer T, Kruhoffer M, Jensen JL, Marcussen N, Hamilton-Dutoit S, Wolf H, and Orntoft TF. Identifying distinct classes of bladder carcinoma using microarrays. Nat Genet 2003;33: 90-6.
Ramaswamy S, Ross KN, Lander ES, and Golub TR. A molecular signature of metastasis in primary solid tumors. Nat Genet 2003;33: 49-54.
Bloom G, Yang IV, Boulware D, Kwong KY, Coppola D, Eschrich S, Quackenbush J, and Yeatman TJ. Multi-platform, multi-site, microarray-based human tumor classification. Am J Pathol 2004;164: 9-16.

(Continued)

*Primary Examiner* — Bin Shen
(74) *Attorney, Agent, or Firm* — Robert J. Varkonyi; Ronald E. Smith; Smith & Hopen, P.A.

(57) ABSTRACT

Here the inventors describe a tumor classifier based on protein expression. Also disclosed is the use of proteomics to construct a highly accurate artificial neural network (ANN)-based classifier for the detection of an individual tumor type, as well as distinguishing between six common tumor types in an unknown primary diagnosis setting. Discriminating sets of proteins are also identified and are used as biomarkers for six carcinomas. A leave-one-out cross validation (LOOCV) method was used to test the ability of the constructed network to predict the single held out sample from each iteration with a maximum predictive accuracy of 87% and an average predictive accuracy of 82% over the range of proteins chosen for its construction.

15 Claims, 18 Drawing Sheets

(56) References Cited

OTHER PUBLICATIONS

Steiner S, Gatlin CL, Lennon JJ, Mcgrath AM, Seonarain MD, Makusky AJ, Aponte AM, Esquerblasco R, and Anderson NL. Cholesterol biosynthesis regulation and protein changes in rat liver following treatment with fluvastatin. Toxicol Lett 2001;120: 369-77.

Gatlin CL, Kleemann GR, Hays LG, Link AJ, and Yates JR, 3rd. Protein identification at the low femtomole level from silver-stained gels using a new fritless electrospray interface for liquid chromatography-microspray and nanospray mass spectrometry. Anal Biochem 1998;263: 93-101.

Kummar S, Fogarasi M, Canova A, Mota A, and Ciesielski T. Cytokeratin 7 and 20 staining for the diagnosis of lung and colorectal adenocarcinoma. Br J Cancer 2002;86: 1884-7.

Cameron RI, Ashe P, O'Rourke DM, Foster H, and McCluggage WG. A panel of immunohistochemical stains assists in the distinction between ovarian and renal clear cell carcinoma. Int J Gynecol Pathol 2003;22: 272-6.

Tothill RW, Kowalczyk A, Rischin D, Bousioutas A, Haviv I, Van Laar RK, Waring PM, Zalcberg J, Ward R, Biankin AV, Sutherland RL, and Henshalli SM, et al. An expression-based site of origin diagnostic method designed for clinical application to cancer of unknown origin. Cancer Res 2005;65: 4031-40.

Petricoin III EF, Ardekani AM, Hitt BA, Levine PJ, Fusaro VA, Steinberg SM, Mills GB, Simone C, Fishman DA, Kohn EC, and Liotta LA. Use of Proteomic Patterns in Serum to Identify Ovarian Cancer. The Lancelot. vol. 359. Feb. 16, 2002.

Conrads TP, Zhou M, Petricoin III EF, Liotta L, and Veenstra TD. Cancer Diagnosis Using Proteomic Patterns. Expert Rev. Mol. Diagn. 3(4), 411-420 (2003).

\* cited by examiner

Exemplary 2-DE Master Gel

ANN Accuracy across Configurations

FIG. 3

Confusion matrix of classification for the ANN showing the highest overall accuracy from the 57 network architectures.

| (a) | (b) | (c) | (d) | (e) | (f) | Classified As/True Class: |
|---|---|---|---|---|---|---|
| 8 | 0 | 1 | 0 | 1 | 0 | (a) OVARY |
| 1 | 7 | 0 | 0 | 1 | 0 | (b) BREAST |
| 0 | 0 | 18 | 0 | 0 | 2 | (c) COLON |
| 0 | 0 | 0 | 10 | 0 | 0 | (d) KIDNEY |
| 0 | 2 | 0 | 0 | 7 | 1 | (e) LUNG |
| 0 | 0 | 1 | 0 | 0 | 17 | (f) STOMACH |

FIG. 4

Percentage Overlap among Proteins Used in ANN

| % overlap | colon | breast | kidney | lung | ovary | stomach |
|---|---|---|---|---|---|---|
| colon | 100.0 | 82.2 | 4.3 | 0.0 | 6.4 | 4.3 |
| breast | 100.0 | 100.0 | 5.7 | 0.0 | 5.7 | 5.7 |
| kidney | 4.1 | 4.1 | 100.0 | 2.0 | 6.1 | 0.0 |
| lung | 0.0 | 0.0 | 3.7 | 100.0 | 3.7 | 3.7 |
| ovary | 9.1 | 6.1 | 9.1 | 3.0 | 100.0 | 15.2 |
| stomach | 5.6 | 5.6 | 0.0 | 2.8 | 13.9 | 100.0 |

Total vs. Unique Proteins for Each Tumor Type

FIG. 6

List of Known Proteins Selected for Ovary Tumors in the ANN Classifier

| Master Spot Number (MSN) | Protein Identified |
|---|---|
| 13 | Vimentin |
| 67 | Lamin B1 |
| 79 | Aldehyde dehydrogenase, mitochondrial precursor (EC 1.2.1.3) (ALDH class 2) (ALDHI) |
| 119 | Lamin B1 |
| 136 | Heteroproteinous nuclear ribonucleoproteins C1/C2 (hnRNP C1 / hnRNP C2) |
| 156 | Pyruvate dehydrogenase E1 component beta subunit, mitochondrial precursor (EC 1.2.4.1) |
| 171 | Glutathione S-transferase P (EC 2.5.1.18) (GST class-pi) (GSTP1-1) |
| 187 | Chloride intracellular channel protein 1 (Nuclear chloride ion channel 27) (NCC27) |
| 205 | Rho GDP-dissociation inhibitor 2 (Rho GDI 2) (Rho-GDI beta) (Ly-GDI) |
| 223 | Rho GDP-dissociation inhibitor 1 (Rho GDI 1) (Rho-GDI alpha) |
| 226 | Mitochondrial intermediate peptidase, mitochondrial precursor (EC 3.4.24.59) (MIP) |
| 229 | Calgranulin B (Migration inhibitory factor-related protein 14) (MRP-14) (P14) |
| 241 | Prohibitin |
| 275 | Heteroproteinous nuclear ribonucleoproteins C1/C2 (hnRNP C1 / hnRNP C2) |
| 400 | Serum albumin precursor |
| 546 | Calgranulin B (Migration inhibitory factor-related protein 14) (MRP-14) (P14)) |
| 861 | Cytosol aminopeptidase (EC 3.4.11.1) (Leucine aminopeptidase) (LAP) |
| 1339 | Tropomyosin 1 alpha chain (Alpha-tropomyosin) |

FIG. 7 List of Known Proteins Selected for Breast Tumors in the ANN Classifier

| Master Spot Number (MSN) | Protein Identified |
|---|---|
| 25 | Collagen alpha 1(VI) chain precursor |
| 25 | Collagen alpha 1(VI) chain precursor |
| 79 | Aldehyde dehydrogenase, mitochondrial precursor (EC 1.2.1.3) (ALDH class 2) (ALDHI) |
| 90 | 150 kDa oxygen-regulated protein precursor (Orp150) (Hypoxia up- regulated 1) |
| 95 | 150 kDa oxygen-regulated protein precursor (Orp150) (Hypoxia up- regulated 1) |
| 111 | 150 kDa oxygen-regulated protein precursor (Orp150) (Hypoxia up- regulated 1) |
| 151 | Annexin A4 (Annexin IV) (Lipocortin IV) (Endonexin I) (Chromobindin 4) (Protein II) |
| 171 | Glutathione S-transferase P (EC 2.5.1.18) (GST class-pi) (GSTP1-1) |
| 173 | Collagen alpha 1(VI) chain precursor |
| 198 | Annexin III (Lipocortin III) (Placental anticoagulant protein III) (PAP-III) |
| 230 | Major vault protein (MVP) (Lung resistance-related protein) |
| 242 | WD-repeat protein 1 (Actin interacting protein 1) (AIP1) (NORI-1) |
| 388 | Ornithine aminotransferase, mitochondrial precursor (EC 2.6.1.13) |
| 477 | Collagen alpha 2(VI) chain precursor |
| 485 | Eukaryotic translation initiation factor 3 subunit 2 (eIF-3 beta) (eIF3 p36) (eIF3i) (TRIP-1) |
| 555 | Monoamine-sulfating phenol sulfotransferase (EC 2.8.2.1) (TL-PST) (HAST3) |
| 606 | 150 kDa oxygen-regulated protein precursor (Orp150) (Hypoxia up- regulated 1) |
| 675 | NADH-ubiquinone oxidoreductase 49 kDa subunit, mitochondrial precursor (EC 1.6.5.3) |
| 779 | Transitional endoplasmic reticulum ATPase (TER ATPase) (15S Mg(2+)-ATPase p97 subunit) |
| 1037 | Apolipoprotein A-IV precursor (Apo-AIV) |
| 1067 | UNR-interacting protein (WD-40 repeat protein PT-WD) (MAP activator with WD repeats) |
| 1504 | Platelet-activating factor acetylhydrolase IB gamma subunit (EC 3.1.1.47) gamma subunit) |

FIG. 8A

List of Known Proteins Selected for Colon Tumors in ANN Classifier

| Master Spot Number (MSN) | Protein Identified |
|---|---|
| 25 | Collagen alpha 1(VI) chain precursor |
| 79 | Aldehyde dehydrogenase, mitochondrial precursor (EC 1.2.1.3) (ALDH class 2) (ALDHI) |
| 90 | 150 kDa oxygen-regulated protein precursor (Orp150) (Hypoxia up- regulated 1) |
| 95 | 150 kDa oxygen-regulated protein precursor (Orp150) (Hypoxia up- regulated 1) |
| 111 | 150 kDa oxygen-regulated protein precursor (Orp150) (Hypoxia up- regulated 1) |
| 151 | Annexin A4 (Annexin IV) (Lipocortin IV) (Endonexin I) (Chromobindin 4) (Protein II) |
| 171 | Glutathione S-transferase P (EC 2.5.1.18) (GST class-pi) (GSTP1-1) |
| 173 | Collagen alpha 1(VI) chain precursor |
| 198 | Annexin III (Lipocortin III) (Placental anticoagulant protein III) (PAP-III) |
| 230 | Major vault protein (MVP) (Lung resistance-related protein) |
| 242 | WD-repeat protein 1 (Actin interacting protein 1) (AIP1) (NORI-1) |
| 388 | Ornithine aminotransferase, mitochondrial precursor (EC 2.6.1.13) |
| 477 | Collagen alpha 2(VI) chain precursor |
| 485 | Eukaryotic translation initiation factor 3 subunit 2 (elF-3 beta) (elF3 p36) (elF3i) (TRIP-1) |

FIG. 8B

List of Known Proteins Selected for Colon Tumors in ANN Classifier (Cont.)

| Master Spot Number (MSN) | Protein Identified |
|---|---|
| 549 | Enoyl-CoA hydratase, mitochondrial precursor (EC 4.2.1.17) (Enoyl-CoA hydratase 1) |
| 552 | Chloride intracellular channel protein 1 (Nuclear chloride ion channel 27) (NCC27) |
| 555 | Monoamine-sulfating phenol sulfotransferase (EC 2.8.2.1) (M-PST) |
| 555 | Monoamine-sulfating phenol sulfotransferase (EC 2.8.2.1) (M-PST) (HAST3) |
| 575 | Myosin regulatory light chain 2, smooth muscle isoform (Myosin RLC) (LC20) |
| 606 | 150 kDa oxygen-regulated protein precursor (Orp150) (Hypoxia up- regulated 1) |
| 620 | Inorganic pyrophosphatase (EC 3.6.1.1) (Pyrophosphate phospho- hydrolase) (PPase) |
| 652 | 14-3-3 protein zeta/delta (Protein kinase C inhibitor protein-1) (KCIP-1) (FAS) |
| 663 | Coatomer beta subunit (Beta-coat protein) (Beta-COP) |
| 675 | NADH-ubiquinone oxidoreductase 49 kDa subunit, mitochondrial precursor (EC 1.6.5.3) |
| 779 | Transitional endoplasmic reticulum ATPase (TER ATPase) (15S Mg(2+)- ATPase |
| 1037 | Apolipoprotein A-IV precursor (Apo-AIV) |
| 1067 | UNR-interacting protein (WD-40 repeat protein PT-WD) (MAP activator with WD repeats) |
| 1504 | Platelet-activating factor acetylhydrolase IB gamma subunit (EC 3.1.1.47) |

FIG. 9A

List of Known Proteins Selected for Kidney Tumors in ANN Classifier

| Master Spot Number (MSN) | Protein Identified |
|---|---|
| 11 | Major vault protein (MVP) (Lung resistance-related protein) |
| 45 | Keratin, type I cytoskeletal 19 (Cytokeratin 19) (K19) (CK 19) |
| 62 | Keratin, type I cytoskeletal 19 (Cytokeratin 19) (K19) (CK 19) |
| 67 | Lamin B1 |
| 105 | Annexin V (Lipocortin V) (Endonexin II) (Calphobindin I) (CBP-I) (PAP-I) (PP4) |
| 136 | Heteroproteinous nuclear ribonucleoproteins C1/C2 (hnRNP C1 / hnRNP C2) |
| 144 | Protein disulfide isomerase A3 precursor (EC 5.3.4.1) (Disulfide isomerase ER-60) |
| 145 | Aldehyde dehydrogenase 1A1 (EC 1.2.1.3) (Aldehyde dehydrogenase, cytosolic) |
| 151 | Annexin A4 (Annexin IV) (Lipocortin IV) (Endonexin I) (Chromobindin 4) (Protein II) |
| 230 | Major vault protein (MVP) (Lung resistance-related protein) |
| 275 | Heteroproteinous nuclear ribonucleoproteins C1/C2 (hnRNP C1 / hnRNP C2) |
| 287 | 14-3-3 protein sigma (Stratifin) (Epithelial cell marker protein 1) |
| 291 | Heat shock 27 kDa protein (HSP 27) (Stress-responsive protein 27) (SRP27) |
| 385 | 3-mercaptopyruvate sulfurtransferase (EC 2.8.1.2) (MST) |
| 405 | Triosephosphate isomerase (EC 5.3.1.1) (TIM) |
| 425 | Fibrinogen beta chain precursor [Contains: Fibrinopeptide B] |
| 461 | Procollagen-lysine,2-oxoglutarate 5-dioxygenase 3 precursor (EC 1.14.11.4) |
| 493 | Stathmin (Phosphoprotein p19) (pp19) (Oncoprotein 18) (Op18) (Metablastin) |

FIG. 9B

List of Known Proteins Selected for Kidney Tumors in ANN Classifier (Cont.)

| Master Spot Number (MSN) | Protein Identified |
|---|---|
| 508 | Aldehyde dehydrogenase 1A1 (EC 1.2.1.3) (Aldehyde dehydrogenase, cytosolic) |
| 526 | Superoxide dismutase [Mn], mitochondrial precursor (EC 1.15.1.1) |
| 535 | Alpha enolase (EC 4.2.1.11) (2-phospho-D-glycerate hydro-lyase) (Non- neural enolase) |
| 558 | Aldehyde dehydrogenase X, mitochondrial precursor (EC 1.2.1.3) (ALDH class 2) |
| 587 | Aspartate aminotransferase, cytoplasmic (EC 2.6.1.1) (Transaminase A) |
| 712 | Phosphoglycerate mutase 1 (EC 5.4.2.1) (EC 5.4.2.4) (EC 3.1.3.13) (PGAM-B) |
| 740 | Proteasome subunit alpha type 6 (EC 3.4.25.1) (Proteasome iota chain) |
| 757 | Heteroproteinous nuclear ribonucleoproteins C1/C2 (hnRNP C1 / hnRNP C2) |
| 789 | Tubulin-specific chaperone A (Tubulin-folding cofactor A) (CFA) |
| 883 | Aldehyde dehydrogenase X, mitochondrial precursor (EC 1.2.1.3) (ALDH class 2) |
| 1017 | Gamma enolase (EC 4.2.1.11) (2-phospho-D-glycerate hydro-lyase) (Neural enolase) |
| 1342 | Aldehyde dehydrogenase 1A1 (EC 1.2.1.3) (Aldehyde dehydrogenase, cytosolic) |
| 1561 | Vimentin |
| 1563 | Tubulin alpha-1 chain (Alpha-tubulin 1) |

FIG. 10

List of Known Proteins Selected for Lung Tumors in the ANN Classifier

| Master Spot Number (MSN) | Protein Identified |
|---|---|
| 37 | 78 kDa glucose-regulated protein precursor (GRP 78) |
| 55 | Protein disulfide isomerase precursor (PDI) (EC 5.3.4.1) (P55) |
| 78 | Calnexin precursor (Major histocompatibility complex class I antigen-binding protein p88) |
| 146 | Macrophage capping protein (Actin-regulatory protein CAP-G) |
| 169 | Cathepsin D precursor (EC 3.4.23.5) |
| 204 | Thymidine phosphorylase precursor (EC 2.4.2.4) (TdRPase) (TP) (PD-ECGF) (Gliostatin) |
| 205 | Rho GDP-dissociation inhibitor 2 (Rho GDI 2) (Rho-GDI beta) (Ly-GDI) |
| 243 | 60 kDa heat shock protein, mitochondrial precursor (Hsp60) (60 kDa chaperonin) (CPN60) |
| 293 | Endoplasmic reticulum protein ERp29 precursor (ERp31) (ERp28) |
| 316 | Protein disulfide isomerase A3 precursor (EC 5.3.4.1) (Disulfide isomerase ER-60) (ERp60) |
| 334 | Keratin, type II cytoskeletal 7 (Cytokeratin 7) (K7) (CK 7) (Sarcolectin) |
| 417 | Elongation factor 1-delta (EF-1-delta) (Antigen NY-CO-4) |
| 425 | Fibrinogen beta chain precursor [Contains: Fibrinopeptide B] |
| 538 | Actin, cytoplasmic 2 (Gamma-actin) |
| 643 | Eukaryotic translation initiation factor 3 subunit 5 (eIF-3 epsilon) (eIF3 p47 subunit) |
| 692 | Alpha enolase (EC 4.2.1.11) (2-phospho-D-glycerate hydro-lyase) (Non- neural enolase) |
| 715 | 2-oxoglutarate dehydrogenase E1 component, mitochondrial precursor (EC 1.2.4.2) |
| 944 | Tryptophanyl-tRNA synthetase (EC 6.1.1.2) (Tryptophan--tRNA ligase) (TrpRS) (IFP53) |

FIG. 11 List of Known Proteins Selected for Stomach Tumors in the ANN Classifier

| Master Spot Number (MSN) | Protein Identified |
|---|---|
| 47 | Serotransferrin precursor (Transferrin) (Siderophilin) (Beta-1-metal binding globulin) |
| 177 | Actin-like protein 3 (Actin-related protein 3) (Actin-2) |
| 229 | Calgranulin B (Migration inhibitory factor-related protein 14) (MRP-14) (P14) |
| 254 | Vimentin |
| 267 | Phosphoglycerate mutase 1 (EC 5.4.2.1) (EC 5.4.2.4) (EC 3.1.3.13) (PGAM-B) |
| 290 | Lamin A/C (70 kDa lamin) |
| 335 | Selenium-binding protein 1 |
| 355 | 14-3-3 protein zeta/delta (Protein kinase C inhibitor protein-1) (KCIP-1) (FAS) |
| 360 | Esterase D (EC 3.1.1.1) |
| 551 | Heteroproteinous nuclear ribonucleoprotein K (hnRNP K) (DC-stretch binding protein) (CSBP) |
| 643 | Eukaryotic translation initiation factor 3 subunit 5 (eIF-3 epsilon) (eIF3 p47 subunit) (eIF3f) |
| 649 | SM_HUMA |
| 727 | Endoplasmin precursor (94 kDa glucose-regulated protein) (GRP94) (gp96 homolog) |
| 822 | Elongation factor 2 (EF-2) |

FIG. 12A

Diagnosis, Subtype and Grade of Ovary Tumors

| Histological Diagnosis | Subtype | Grade |
|---|---|---|
| Adenocarcinoma | Papillary Serous Cystadeno | moderately differentiated |
| Adenocarcinoma | Papillary Serous Cystadeno | moderately differentiated |
| Adenocarcinoma | Papillary Serous Cystadeno | moderately differentiated |
| Adenocarcinoma | Papillary Serous Cystadeno | moderately differentiated |
| Adenocarcinoma | Mucinous Cystadeno | moderately differentiated |
| Adenocarcinoma | Papillary Serous Cystadeno | moderately differentiated |
| Adenocarcinoma | Papillary Serous Cystadeno | well differentiated |
| Adenocarcinoma | Mucinous Cystadeno | moderately differentiated |
| Adenocarcinoma | Papillary Serous Cystadeno | moderately differentiated |
| Adenocarcinoma | Papillary Serous Cystadeno | moderately differentiated |

FIG. 12B

Diagnosis, Subtype and Grade of Breast Tumors

| Histological Diagnosis | Subtype | Grade |
|---|---|---|
| Adenocarcinoma | Infiltrating Ductal Carcinoma | moderately differentiated |
| Adenocarcinoma | Infiltrating Ductal Carcinoma | moderately differentiated |
| Adenocarcinoma | Infiltrating Ductal Carcinoma | moderately differentiated |
| Adenocarcinoma | Infiltrating Ductal Carcinoma | moderately differentiated |
| Adenocarcinoma | Infiltrating Ductal Carcinoma | moderately differentiated |
| Adenocarcinoma | Infiltrating Ductal Carcinoma | moderately differentiated |
| Adenocarcinoma | Infiltrating Ductal Carcinoma | moderately differentiated |
| Adenocarcinoma | Infiltrating Ductal Carcinoma | moderately differentiated |
| Adenocarcinoma | Lobular Carcinoma | moderately differentiated |

FIG. 12C

Diagnosis, Subtype and Grade of Colon Tumors

| Histological Diagnosis | Subtype | Grade |
|---|---|---|
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |
| Adenocarcinoma | Invasive | moderately differentiated |

FIG. 12D

Diagnosis, Subtype and Grade of KidneyTumors

| Histological Diagnosis | Subtype | Grade |
|---|---|---|
| Adenocarcinoma | Clear Cell Type | moderately differentiated |
| Adenocarcinoma | Clear Cell Type | moderately differentiated |
| Adenocarcinoma | Clear Cell Type | moderately differentiated |
| Adenocarcinoma | Papillary Type | moderately differentiated |
| Adenocarcinoma | Clear Cell Type | moderately differentiated |
| Adenocarcinoma | Clear Cell Type | moderately differentiated |
| Adenocarcinoma | Clear Cell Type | moderately differentiated |
| Adenocarcinoma | Clear Cell Type | moderately differentiated |
| Adenocarcinoma | Clear Cell Type | moderately differentiated |
| Adenocarcinoma | Clear Cell Type | moderately differentiated |

FIG. 12E

Diagnosis, Subtype and Grade of Lung Tumors

| Histological Diagnosis | Subtype | Grade |
|---|---|---|
| Adenocarcinoma | | moderately differentiated |
| Adenocarcinoma | | moderately differentiated |
| Adenocarcinoma | | moderately differentiated |
| Adenocarcinoma | | poorly differentiated |
| Adenocarcinoma | Non Small Cell | moderately differentiated |
| Adenocarcinoma | Non Small Cell | moderately differentiated |
| Adenocarcinoma | | moderately differentiated |
| Adenocarcinoma | | moderately differentiated |
| Adenocarcinoma | | moderately differentiated |
| Adenocarcinoma | | poorly differentiated |

FIG. 12F

Diagnosis, Subtype and Grade of Stomach Tumors

| Histological Diagnosis | Subtype | Grade |
|---|---|---|
| Adenocarcinoma | Signet Ring | poorly differentiated |
| Adenocarcinoma | diffuse | poorly differentiated |
| Adenocarcinoma | Intestinal Type | moderately differentiated |
| Adenocarcinoma | Intestinal Type | moderately differentiated |
| Adenocarcinoma | Intestinal Type | moderately differentiated |
| Adenocarcinoma | diffuse | poorly differentiated |
| Adenocarcinoma | Intestinal Type | moderately differentiated |
| Adenocarcinoma | diffuse | poorly differentiated |
| Adenocarcinoma | Intestinal Type | moderately differentiated |
| Adenocarcinoma | Signet Ring | poorly differentiated |
| Adenocarcinoma | Intestinal Type | moderately differentiated |
| Adenocarcinoma | diffuse | poorly differentiated |
| Adenocarcinoma | Intestinal Type | moderately differentiated |
| Adenocarcinoma | Signet Ring | poorly differentiated |
| Adenocarcinoma | diffuse | poorly differentiated |
| Adenocarcinoma | Intestinal Type | moderately differentiated |
| Adenocarcinoma | Intestinal Type | moderately differentiated |
| Adenocarcinoma | Intestinal Type | moderately differentiated |

ARTIFICIAL NEURAL NETWORK PROTEOMIC TUMOR CLASSIFICATION

CROSS REFERENCE TO RELATED DISCLOSURES

This application claims priority Provisional Patent Application No. 60/822,148, filed Aug. 11, 2006 which is incorporated herein by reference.

GOVERNMENT SUPPORT

This invention was made with Government support under Grant No. U01CA85052 awarded by the National Cancer Institute. The Government has certain rights in the invention.

FIELD OF INVENTION

This invention relates to the field of cancer therapy.

BACKGROUND OF THE INVENTION

Precise tumor diagnosis is the first step in cancer management since therapy generally stems from the initial tumor classification. While many tumor biopsies are diagnostic and form the cornerstone of cancer therapy, classification of tumor type and site of origin is a significant clinical challenge that is often under-estimated. Distinguishing the most common metastatic adenocarcinomas (ovary, colon, kidney, breast, lung and stomach) from each other is one of the most vexing problems facing clinicians today. In fact, it is estimated that up to 10% of all metastatic tumors have no defined primary site of origin. Moreover, adenocarcinomas represent 60% of all of unknown primary tumor types. The current standard of pathologic practice, using morphologic criteria and semi-quantitative immunohistochemical (IHC) analyses, is often limited in its capacity to define tumor type or site of origin. Thus, there is a clear need for the identification and validation of a classification model that will cleanly distinguish these histologically similar tumor types and improve the inventor's capacity to direct therapy.

Gene expression profiling is a powerful tool that has shown promise in its capacity to discriminate subpopulations of tumors from heterogeneous groups. The inventors recently developed a prototype multi-tumor classifier capable of interrogating up to 21 different tumor types with an accuracy of ~88%. (see Bloom G, Yang I V, Boulware D, Kwong K Y, Coppola D, Eschrich S, Quackenbush J, Yeatman T J. Multi-platform, multi-site, microarray-based human tumor classification. *Am J Pathol* 2004; 164: 9-16; which is incorporated herein by reference).

SUMMARY OF INVENTION

Pathologists are commonly faced with the problem of attempting to identify the site of origin of a metastatic cancer when no primary tumor has been identified, yet few markers have been identified to date. Here the invention includes a tumor classifier based entirely on protein expression quantified by two-dimensional gel electrophoresis (2DE). 2DE was used to analyze the proteomic expression pattern of 77 similarly appearing (using histomorphology) adenocarcinomas encompassing six types or sites of origin: ovary, colon, kidney, breast, lung and stomach. Discriminating sets of proteins were identified and used to train an artificial neural network (ANN). A leave-one-out cross validation (LOOCV) method was used to test the ability of the constructed network to predict the single held out sample from each iteration with a maximum predictive accuracy of 87% and an average predictive accuracy of 82% over the range of proteins chosen for its construction. These findings demonstrate the use of proteomics to construct a highly accurate ANN-based classifier for the detection of an individual tumor type, as well as distinguishing between six common tumor types in an unknown primary diagnosis setting.

Using 2-D gel analysis combined with MALDI mass spectrometry to simultaneously assess 1400 protein spots, the inventors developed global protein expression profiles for 77 primary adenocarcinomas representing six different organ sites. The inventors used a series of Wilcoxon Rank-Sum tests to generate six lists of proteins that effectively separated their associated tumors from the other five tumor types. A neural network was then constructed to develop a classifier to identify all six tumor types with a high degree of overall accuracy in a leave-one-out cross validation (LOOCV). Proteins have been identified by mass spectrometry that may serve as novel biomarkers for each disease site.

In one embodiment, the invention includes a method of determining the site of origin, within a subject, of a neoplasm by establishing a protein expression profile of multiple, known neoplasms (such as metastatic neoplasms and tumors). A sample containing a neoplasm of unknown origin is then obtained from the subject and a protein expression profile is established for the sample. The protein expression profile for the sample is then compared to the protein expression profile of known neoplasms to see if there is a match between the two profiles. In one embodiment the known neoplasms originate in the ovary, colon, kidney, breast, lung and/or stomach.

In a preferred embodiment, the protein expression profile for the sample is compared to the protein expression profile of the known neoplasms using an artificial neural network. The respective protein profiles are compared using a leave-one-out cross validation algorithm.

In another embodiment, the invention includes a method of determining the site of origin, within a subject, of a neoplasm by providing a protein expression profile of multiple, known neoplasm, each neoplasm containing at least one biomarker. A sample containing a neoplasm of unknown origin is then obtained from the subject and a protein expression profile is established for the sample. The protein expression profile for the sample is then compared to the protein expression profile of the known neoplasms to detect the presence of a biomarker from the protein expression profile of the known neoplasms in the protein expression profile for the sample.

In another embodiment, the invention includes a method of determining the site of origin, within a subject, of a neoplasm by obtaining a sample of the neoplasm from the subject and detecting, within the sample, the presence of a biomarker which correlates with a biomarker in a neoplasm of the ovary, colon, kidney, breast, lung and/or stomach.

In another embodiment, the invention includes a series of biomarkers of a neoplasm having a site of origin in the colon. The biomarker of this embodiment is a protein selected from the group consisting of Enoyl-CoA hydratase, mitochondrial precursor (EC 4.2.1.17) (Enoyl-CoA hydratase 1), Chloride intracellular channel protein 1 (Nuclear chloride ion channel 27) (NCC27), Myosin regulatory light chain 2, smooth muscle isoform (Myosin RLC) (LC20), Inorganic pyrophosphatase (EC 3.6.1.1) (Pyrophosphate phospho-hydrolase) (PPase), 14-3-3 protein zeta/delta (Protein kinase C inhibitor protein-1) (KCIP-1) (FAS), and Coatomer beta subunit (Beta-coat protein) (Beta-COP).

In another embodiment, the invention includes a series of biomarkers of a neoplasm having a site of origin in the breast. The biomarker of this embodiment is a protein selected from the group consisting of Collagen alpha 1(VI) chain precursor, Collagen alpha 1(VI) chain precursor, Aldehyde dehydrogenase, mitochondrial precursor (EC 1.2.1.3) (ALDH class 2) (ALDHI), 150 kDa oxygen-regulated protein precursor (Orp150) (Hypoxia up-regulated 1), 150 kDa oxygen-regulated protein precursor (Orp150) (Hypoxia up-regulated 1), 150 kDa oxygen-regulated protein precursor (Orp150) (Hypoxia up-regulated 1), Annexin A4 (Annexin IV) (Lipocortin IV) (Endonexin I) (Chromobindin 4) (Protein II), Glutathione S-transferase P (EC 2.5.1.18) (GST class-pi) (GSTP1-1), Collagen alpha 1(VI) chain precursor, Annexin III (Lipocortin III) (Placental anticoagulant protein III) (PAP-III), Major vault protein (MVP) (Lung resistance-related protein), WD-repeat protein 1 (Actin interacting protein 1) (AIP1) (NORI-1), Ornithine aminotransferase, mitochondrial precursor (EC 2.6.1.13), Collagen alpha 2(VI) chain precursor, Eukaryotic translation initiation factor 3 subunit 2 (eIF-3 beta) (eIF3 p36) (eIF31) (TRIP-1), Monoamine-sulfating phenol sulfotransferase (EC 2.8.2.1) (TL-PST) (HAST3), 150 kDa oxygen-regulated protein precursor (Orp150) (Hypoxia up-regulated 1), NADH-ubiquinone oxidoreductase 49 kDa subunit, mitochondrial precursor (EC 1.6.5.3), Transitional endoplasmic reticulum ATPase (TER ATPase) (15S Mg(2+)-ATPase p97 subunit), Apolipoprotein A-IV precursor (Apo-AIV), UNR-interacting protein (WD-40 repeat protein PT-WD) (MAP activator with WD repeats), and Platelet-activating factor acetylhydrolase IB gamma subunit (EC 3.1.1.47) gamma subunit)

In another embodiment, the invention includes a series of biomarkers of a neoplasm having a site of origin in the kidney. The biomarker of this embodiment is a protein selected from the group consisting of Major vault protein (MVP) (Lung resistance-related protein), Keratin, type I cytoskeletal 19 (Cytokeratin 19) (K19) (CK 19), Keratin, type I cytoskeletal 19 (Cytokeratin 19) (K19) (CK 19), Annexin V (Lipocortin V) (Endonexin II) (Calphobindin I) (CBP-I) (PAP-I) (PP4), Protein disulfide isomerase A3 precursor (EC 5.3.4.1) (Disulfide isomerase ER-60), Aldehyde dehydrogenase 1A1 (EC 1.2.1.3) (Aldehyde dehydrogenase, cytosolic), 14-3-3 protein sigma (Stratifin) (Epithelial cell marker protein 1), Heat shock 27 kDa protein (HSP 27) (Stress-responsive protein 27) (SRP27), 3-mercaptopyruvate sulfurtransferase (EC 2.8.1.2) (MST), Triosephosphate isomerase (EC 5.3.1.1) (TIM), Procollagen-lysine, 2-oxoglutarate 5-dioxygenase 3 precursor (EC 1.14.11.4), Stathmin (Phosphoprotein p19) (pp 19) (Oncoprotein 18) (Op18) (Metablastin), Aldehyde dehydrogenase 1A1 (EC 1.2.1.3) (Aldehyde dehydrogenase, cytosolic), Superoxide dismutase [Mn], mitochondrial precursor (EC 1.15.1.1), Alpha enolase (EC 4.2.1.11) (2-phospho-D-glycerate hydro-lyase) (Non-neural enolase), Aldehyde dehydrogenase X, mitochondrial precursor (EC 1.2.1.3) (ALDH class 2), Aspartate aminotransferase, cytoplasmic (EC 2.6.1.1) (Transaminase A), Phosphoglycerate mutase 1 (EC 5.4.2.1) (EC 5.4.2.4) (EC 3.1.3.13) (PGAM-B), Proteasome subunit alpha type 6 (EC 3.4.25.1) (Proteasome iota chain), Heteroproteinous nuclear ribonucleoproteins C1/C2 (hnRNP C1/hnRNP C2), Tubulin-specific chaperone A (Tubulin-folding cofactor A) (CFA), Aldehyde dehydrogenase X, mitochondrial precursor (EC 1.2.1.3) (ALDH class 2), Gamma enolase (EC 4.2.1.11) (2-phospho-D-glycerate hydro-lyase) (Neural enolase), Aldehyde dehydrogenase 1A1 (EC 1.2.1.3) (Aldehyde dehydrogenase, cytosolic) and Tubulin alpha-1 chain (Alpha-tubulin 1).

In another embodiment, the invention includes a series of biomarkers of a neoplasm having a site of origin in the lung. The biomarker of this embodiment is a protein selected from the group consisting of 78 kDa glucose-regulated protein precursor (GRP 78), Protein disulfide isomerase precursor (PDI) (EC 5.3.4.1) (P55), Calnexin precursor (Major histocompatibility complex class I antigen-binding protein p88), Macrophage capping protein (Actin-regulatory protein CAP-G), Cathepsin D precursor (EC 3.4.23.5), Thymidine phosphorylase precursor (EC 2.4.2.4) (TdRPase) (TP) (PD-ECGF) (Gliostatin), Rho GDP-dissociation inhibitor 2 (Rho GDI 2) (Rho-GDI beta) (Ly-GDI), 60 kDa heat shock protein, mitochondrial precursor (Hsp60) (60 kDa chaperonin) (CPN60), Endoplasmic reticulum protein ERp29 precursor (ERp31) (ERp28), Protein disulfide isomerase A3 precursor (EC 5.3.4.1) (Disulfide isomerase ER-60) (ERp60), Keratin, type II cytoskeletal 7 (Cytokeratin 7) (K7) (CK 7) (Sarcolectin), Elongation factor 1-delta (EF-1-delta) (Antigen NY-CO-4), Fibrinogen beta chain precursor [Contains: Fibrinopeptide B], Actin, cytoplasmic 2 (Gamma-actin), Eukaryotic translation initiation factor 3 subunit 5 (eIF-3 epsilon) (eIF3 p47 subunit), Alpha enolase (EC 4.2.1.11) (2-phospho-D-glycerate hydro-lyase) (Non-neural enolase), 2-oxoglutarate dehydrogenase E1 component, mitochondrial precursor (EC 1.2.4.2) and Tryptophanyl-tRNA synthetase (EC 6.1.1.2) (Tryptophan—tRNA ligase) (TrpRS) (IFP53).

In another embodiment, the invention includes a series of biomarkers of a neoplasm having a site of origin in the ovary. The biomarker of this embodiment is a protein selected from the group consisting of Lamin B1, Pyruvate dehydrogenase E1 component beta subunit, mitochondrial precursor (EC 1.2.4.1), Chloride intracellular channel protein 1 (Nuclear chloride ion channel 27) (NCC27), Rho GDP-dissociation inhibitor 1 (Rho GDI 1) (Rho-GDI alpha), Mitochondrial intermediate peptidase, mitochondrial precursor (EC 3.4.24.59) (MIP), Prohibitin, Serum albumin precursor, Calgranulin B (Migration inhibitory factor-related protein 14) (MRP-14) (P14)), Cytosol aminopeptidase (EC 3.4.11.1) (Leucine aminopeptidase) (LAP), and Tropomyosin 1 alpha chain (Alpha-tropomyosin).

In another embodiment, the invention includes a series of biomarkers of a neoplasm having a site of origin in the stomach. The biomarker of this embodiment is a protein selected from the group consisting of Serotransferrin precursor (Transferrin) (Siderophilin) (Beta-1-metal binding globulin), Actin-like protein 3 (Actin-related protein 3) (Actin-2), Vimentin, Phosphoglycerate mutase 1 (EC 5.4.2.1) (EC 5.4.2.4) (EC 3.1.3.13) (PGAM-B), Lamin A/C (70 kDa lamin), Selenium-binding protein 1, 14-3-3 protein zeta/delta (Protein kinase C inhibitor protein-1) (KCIP-1) (FAS), Esterase D (EC 3.1.1.1), Heteroproteinous nuclear ribonucleoprotein K (hnRNP K) (DC-stretch binding protein) (CSBP) and SM_HUMA, Endoplasmin precursor (94 kDa glucose-regulated protein) (GRP94) (gp96 homolog).

BRIEF DESCRIPTION OF THE DRAWINGS

For a fuller understanding of the invention, reference should be made to the following detailed description, taken in connection with the accompanying drawings, in which:

FIG. 3 is the confusion matrix of classification for the ANN showing the highest overall accuracy from 57 ANN architectures.

FIG. 4 is a table showing the percentage overlap among the proteins used in the ANN.

FIG. 6 is a table of the known proteins selected for ovary tumors; unique proteins for ovary tumors are shown in bold.

FIG. 7 is a table of the known proteins selected for breast tumors; unique proteins for breast tumors are shown in bold.

FIG. 8A and FIG. 8B are tables of the known proteins selected for colon tumors; unique proteins for colon tumors are shown in bold.

FIG. 9A and FIG. 9B are tables of the known proteins selected for kidney tumors; unique proteins for kidney tumors are shown in bold.

FIG. 10 is a table of the known proteins selected for lung tumors; unique proteins for lung tumors are shown in bold.

FIG. 11 is a table of the known proteins selected for stomach tumors; unique proteins for stomach tumors are shown in bold.

FIG. 12A is a table showing the diagnosis, subtype and grade of ovary tumors.

FIG. 12B is a table showing the diagnosis, subtype and grade of breast tumors (infiltrating ductal and lobular carcinoma subtype).

FIG. 12C is a table showing the diagnosis, subtype and grade of colon tumors.

FIG. 12D is a table showing the diagnosis, subtype and grade of kidney tumors.

FIG. 12E is a table showing the diagnosis, subtype and grade of breast tumors (non small cell subtype).

FIG. 12F is a table showing the diagnosis, subtype and grade of stomach tumors.

DETAILED DESCRIPTION OF THE PREFERRED EMBODIMENT

Figure 1:
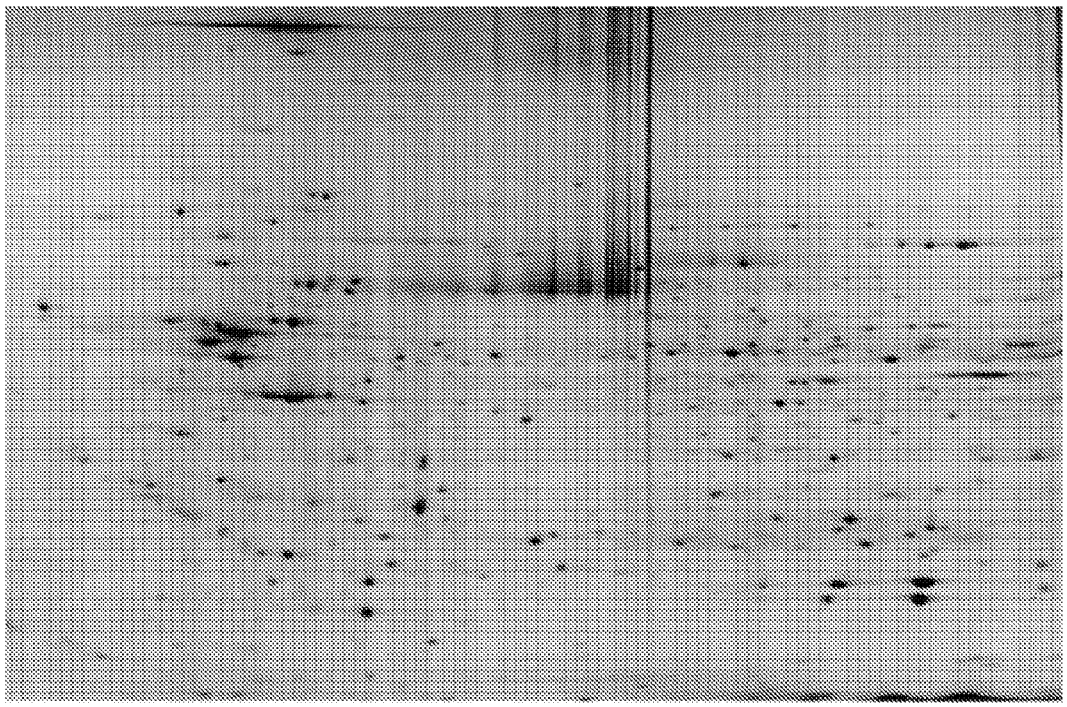
FIG. 1 is a representative 2-DE gel used as the master gel for spot matching in this study. Protein sample from kidney Adenocarcinoma was prepared and 2-DE was performed as described in the Materials and Methods section. The pI (4 to 7) and the molecular weight were calibrated using Kepler® software. About 1400 protein spots were analyzed for each gel using Kepler® software.

A number of adenocarcinomas still produce significant diagnostic challenges to pathologists and practicing clinicians. The unknown primary cancer, often a metastatic adenocarcinoma to sites like the liver or lungs, represents a substantial number of cases worldwide and is highly problematic. Similarly, discriminating primary tumors from organs such as the ovary versus the colon can be difficult. Since therapy still stems from the organ site-based diagnosis, correct identification of site of origin of cancer is clinically valuable. To address these problems, the inventors have profiled a significant number of human tumors using a global protein approach. The inventors have constructed an ANN, protein-based classifier that is very accurate as assessed by LOOCV in the classification of six common tumor types: lung, kidney, breast, colon, ovary, and stomach. A series of Wilcoxon Rank-Sum tests were used to identify a discriminating set of proteins. The use of this one vs. all approach coupled with the inventor's selection method, while simple in application, was key in the inventor's ability to construct a successful classifier and allowed us to test for proteins that separated a single group from all remaining classes. Most importantly, this approach prevented the selection of a group of features that, although being the most statistically significant, contained a large number of proteins that discriminated one type of tumor from only one or a few of the other types.

Analysis of the selected proteins revealed the value of this approach as most of the tumor classes shared only a small percentage of proteins selected. The exception was breast and colon, where all breast proteins were also contained in the colon set. The multi-tumor classifier, however, was still able to successfully separate these two groups. The most likely explanation was that, although they both shared the same proteins, the levels of protein were differentiating enough for correct classification. The invention is also useful in data analysis involving high dimensional multi-class data, a global problem in bioinformatics and proteomics in particular.

In addition to the unique feature selection approach, the inventors examined the effect of ANN architecture on its ability to correctly classify the six tumor types. This was done by using an automated scripting approach that generated a series of networks with increasing numbers of input nodes and differing numbers of hidden nodes. In all, 57 networks were constructed, trained, and tested using a LOOCV approach. This analysis allowed us to determine the correct architecture for use in the inventor's classifier.

In the inventor's work using microarray data (supra) the inventors were successfully able to identify metastatic tumors starting with primaries as well as identifying primaries when the classifier was built using metastatic tumors. In addition, it is possible to classify metastasis of unknown origin using a cDNA based SVM classifier constructed with data from 13 primary tumor types. (see Tothill R W, Kowalczyk A, Rischin D, Bousioutas A, Haviv I, van Laar R K, Waring P M, Zalcberg J, Ward R, Biankin A V, Sutherland R L, Henshall S M, et al. An expression-based site of origin diagnostic method designed for clinical application to cancer of unknown origin. *Cancer Res* 2005; 65: 4031-40; which is incorporated herein by reference). These results from the microarray field validate the use of proteomic data from primary tumors to develop an accurate classifier to address the important unknown primary problem in cancer diagnosis.

As used herein, the term "neoplasm" is the abnormal proliferation of the cells of a tissue or organ. The term "neoplasm" also refers to a growth formed as a result of the abnormal proliferation of the cells of a tissue or organ.

As used herein, the term "biomarker" refers to a molecule, such as a protein, that allows for the detection and isolation of a particular cell type. The molecule serves, or can serve, as a marker for a particular normal or abnormal property of a cell or organism, such as response to a drug treatment, a bioactive agent treatment or as a marker for particular or general physiological states, e.g., normal, abnormal, or pathological.

As used herein, the term "protein expression profile" refers to an indication of the expression extent or abundance values for a part, or all, of the proteins or polypeptides present in a sample population. For example, a protein expression profile for a given protein population, such as a cell, indicates the proteins which are detectable as expressed and those which are not detectable as expressed. A protein expression profile can provide a quantitative measure of the extent, either absolute or relative, of expression for one or more proteins. The expression profiles of two or more sample protein populations can be compared to identify differences in expression extents, which exist between the different samples. Methods of establishing Protein Expression Profiles are known in the art. For example, see U.S. Patent Application Publication 2005/0, 048,564 to Emili et. al. and U.S. Patent Application Publication 2007/0,111,257 to Kohne; which are incorporated herein by reference.

As used herein, an artificial neural network (ANN), is a mathematical or computational model based on a biological neural network. In one embodiment, the ANN is an adaptive system that changes its structure based on external or internal information that flows through the network during a learning phase.

Protein Separation and Identification

A total of 77 primary adenocarcinoma tissue samples were analyzed. For each sample, at least three gels were run and the gel with the best quality was chosen to represent that sample for the subsequent analysis. The reproducibility of the gels for each sample was examined by measuring the coefficient of variation (CV) of selected 100 protein spots from those gels. A distribution of CV was plotted for each sample. For most samples, more than 80% of the spots had CV≤10%. About 1400 protein spots were visualized following staining of 2D gels. FIG. 1 shows a typical 2DE image produced from a human kidney cancer specimen. The edited Master Pattern USF209M2 contains 1420 proteins spots covering the protein spots across all the 77 patterns. Using MALDI or LC-MS/MS, 650 protein spots were identified. Based on the pI and molecular weight (MW) information from the identified protein spots, each 2DE pattern was calibrated for its pI (4-7) and MW ranges. Results of mass spectrometry analysis produced identification for 69 of the 173 unique proteins selected from the ANN with inputs ranging between 330 and 570. Only protein abundances were assessed. Occasionally, multiple protein identifications of the same protein were observed and could represent identical isoforms or could also represent subtle differences based on post-translational modifications such as glycosylation or phosphorylation or even partial degradation.

ANN Results

Figure 2:
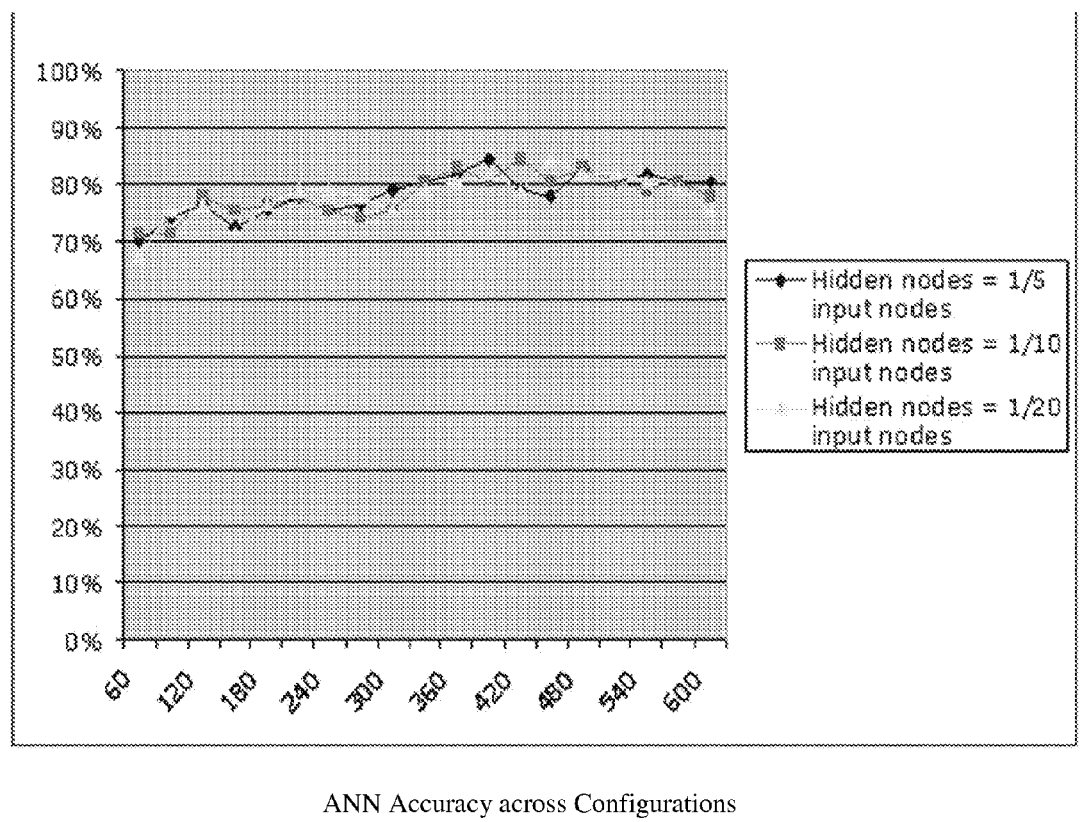
FIG. 2 is a graph showing Artificial Neural Network (ANN) accuracy across various network configurations. Y axis is percentage accuracy for the network—X axis is the number of input nodes i.e. the number of proteins used in the ANN. The number of hidden nodes for each of the network constructs were derived using a formula where hidden nodes=1/x (input nodes) where x=5, 10, and 20.

FIG. 2 is a summary of the accuracies of all 57 different ANN architectures. As can be seen the figure, the accuracy of the network on the left out sample trends upward as the number of inputs increase, until the number of inputs approaches 540. The increase of accuracy reflects the increase of information contained in the proteins as they are added to the ANN. Once the amount of noise in the additional proteins outweighs the information content, the network performance suffers. It is also important to note that the number of hidden units as a function of input nodes seemed to have little effect on the overall network accuracy. The accuracy of the ANN, when given enough proteins for classification, is 87% with a mean accuracy of 82% across all configurations. Due to the limited sample numbers, an independent test approach could not be used for this study. As can be seen from the confusion matrix (FIG. 3), the incorrectly classified samples were fairly well distributed equally across all the tumor types demonstrating the network performed equally well at classifying all six tumor types. This result is comparable to previous work using microarray technology and represents a potential new approach to tumor classification of unknown primary cancers. (see Bloom G, Yang I V, Boulware D, Kwong K Y, Coppola D, Eschrich S, Quackenbush J, Yeatman T J. Multi-platform, multi-site, microarray-based human tumor classification. *Am J Pathol* 2004; 164: 9-16; which is incorporated herein by reference).

Description of Selected Proteins

Figure 5:
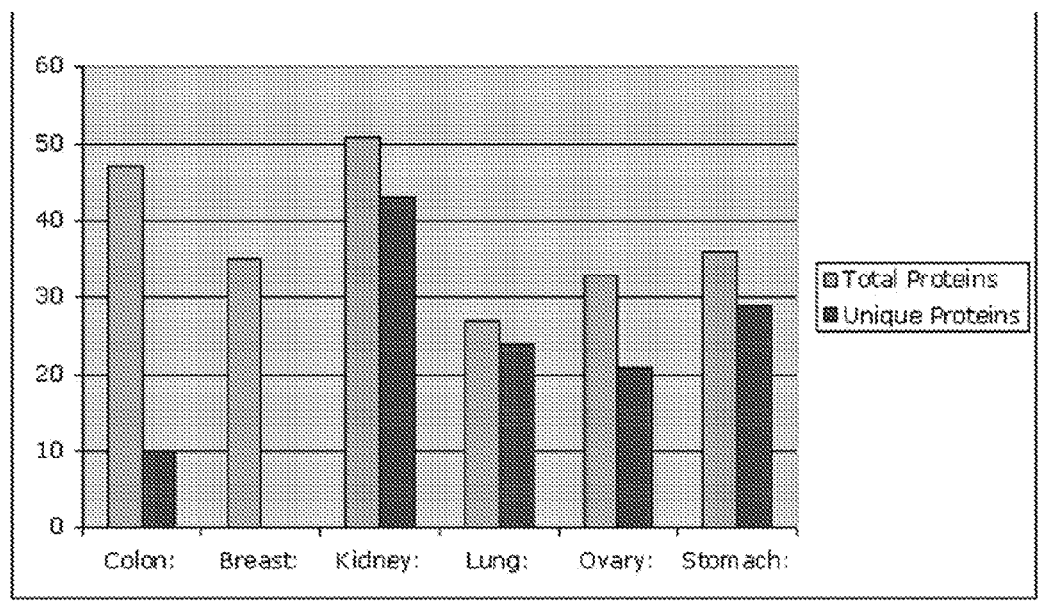
FIG. 5 is a histogram of total vs. unique proteins used per tumor type in the ANN unknown primary classier. Y-axis is the number of proteins, X-axis is the tumor type.

Analysis was performed in order to gain insight into the proteins selected by the inventor's approach for each of the six classes. FIG. 4 details the percentage of proteins selected that were unique to each of the tumors. Surprisingly, the proteins selected for distinguishing breast cancer from all other tumor types were also present in the colon vs. all set. Not surprising, however, was the relatively low amount of overlap between kidney and the other five tumor types, reflecting the uniqueness of kidney tumors in general. Of the six types of adenocarcinomas represented in this study, kidney adenocarcinomas were the most histologically distinct. For the majority of tumor types, the percentage of proteins selected for other tumors ranged from 3 to 10%. FIG. 5 is a histogram summary of the number of discriminating proteins identified vs. the number of those proteins that were unique to that tumor.

A total of 1412 proteins were used in the selection process. Proteins were selected based on differences in protein abundance rather than based on other potential differences such as those induced by post-translational modification, which were not measured. The inventors identified 227 total proteins when selecting those artificial neural network architectures containing between 330 and 570 input nodes. Of these, 173 proteins were unique to individual tumor types. From this set, 69 have had their identities confirmed via mass spectrometry. FIGS. 6 through 11 include tables listing identified proteins for each of their respective classes with the unique proteins for each class shown in bold. These proteins represent candidate tumor biomarkers for each tumor type.

Clinical Samples

Human tumor samples were obtained from the Moffitt Cancer Center Tumor Bank under IRB approved protocols. Seventy-seven primary tumor samples were obtained from six different sites of origin. In addition, tumors with all differentiation statuses were used to help insure that any potential classifier would serve in a realistic clinical setting. All samples were obtained within 15 minutes of surgical extirpation and snap frozen in liquid nitrogen. Tumor samples were then microdissected to >80% purity prior to protein extraction under frozen section control. Laser capture microdissection (LCM) was not applied to the samples as the inventors wanted to include stromal elements that the inventors believe add critical signature information derived from the tumor cells interacting with their environment. Samples were distributed among six organ sites as follows: 10 ovary (FIG. 12A); 9 breast (FIG. 12B); 20 colon (FIG. 12C); 10 kidney (FIG. 12D); 10 lung (FIG. 12E); and 18 stomach (FIG. 12F).

Sample Preparation

Tumor samples were homogenized in eight volumes of 9M urea, 2% CHAPS, 0.5% dithiothreitol (DTT) and 2% carrier ampholytes pH 8-10.5. The homogenates were centrifuged at 420,000×g at 22° C. for 40 min (Optima™ L70-K ultracentrifuge, Type 50.4 Ti rotor, 50,000 rpm; Beckman Instruments, Palo Alto, Calif.). The supernatant was removed, divided into four aliquots and stored at −80° C. until analysis.

Two-Dimensional Gel Electrophoresis

Sample proteins were resolved using the ISO-200 and the DALT-100 components of LSBC's fully automated ProGEx™ system. The protein concentration of the tumor samples were measured using the BCA method in the absence of ampholytes. About 200 μg of solubilized sample were applied to each gel, and the gels were run in groups of 25 for 25,050 volt-hours using a logarithmically increasing voltage with a high-voltage programmable power supply. An Angelique™ computer-controlled gradient-casting system (Large Scale Biology Corporation, Germantown, Md.) was used to prepare the second-dimension SDS slab gels. The top 5% of each gel was 8% T acrylamide and the lower 95% of the gel varied linearly from 8% to 15% T. The IEF gels were loaded directly onto the slab gels using an equilibration buffer with a blue tracking dye and were held in place with a 1% agarose overlay. Second-dimensional 20×25 cm slab gels were run in groups of 25, with a run time of 2 hours at 600 V in cooled DALT tanks (20° C.) with buffer circulation, and were taken out when the tracking dye reached the bottom of the gel. Following SDS electrophoresis, the slab gels were fixed overnight in 1.5 liters/10 gels of 50% ethanol/3% phosphoric acid and then washed three times for 30 min in 1.5 liters/10 gels of temperate DI water. They were transferred to 1.5 liters/10 gels of 34% methanol/17% ammonium sulfate/3% phosphoric acid for one hour, and after the addition of one gram powdered Coomassie Blue G-250 the gels were stained for three days to achieve equilibrium intensity.

Quantitative Gel Pattern Analysis

Stained slab gels were digitized in red light at 100 micron resolution, using an Ektron 1412 scanner and images were processed using the Kepler® software system. A master pattern (USF209M2) was constructed from one of the best quality patterns and edited to include spots observed from all of the tissues. Three gels were run for each of the 77 tissue samples. The criteria for choosing the best gel to represent each sample included that the gel had the least horizontal and/or vertical streaking, no or very low staining background, and no broken pieces. An experiment package was constructed using the best 2DE pattern of each tissue sample, and each pattern was matched to the USF209M2 master to establish the correspondence of spots between patterns and to assign master numbers to spots. The pattern matching process included manual and automatic procedures. The single master gave adequate representation for all of the tissues and allowed all of the patterns to be matched together as a single unit, greatly simplifying the analysis. To correct for differences in loading and staining, the 77 patterns were scaled together by a linear procedure based on a selected set of spots by setting the summed abundance of the selected spots equal to a constant (linear scaling).

Sample Preparation for Protein Spot Analysis by Mass Spectrometry

Protein spots were excised from Coomassie stained gels using an LSBC-designed, fully automated proprietary spot cutter and placed in a 96-well polypropylene microtiter plate for further processing. Sample preparation of gel plugs (destain, reduction and alkylation, trypsin digestion) was carried out on a TECAN Genesis Workstation 200 (Tecan, Durham, N.C.) equipped with a carousel tower, a ROMA microtiter plate transport arm, a LIHA 8-tip liquid handler arm and 4 hotels for incubation in the dark at room temperature and at 37° C. The TECAN was controlled by two interactive pieces of software: Gemini software controlled the liquid handling and FACTS software controlled the scheduling. A similar sample preparation method described previously was used. Briefly, gel plugs were destained by two 45-min cycles of 0.1M $NH_4HCO_3$ (AmBic) in 50% $CH_3CN$. Wash was discarded. Reduction and alkylation were accomplished by dispensing 400 nmol DTT in 0.1M AmBic and incubating at 37° C. for 30 min in the dark. After cooling, 2.2 mmol iodoacetamide in 0.1M AmBic was added and incubated at room temperature (RT) in the dark for 30 min. The supernatant was removed, and spots were washed with diHOH, then 100% MeCN was added and discarded after 15 min to dehydrate gel plugs. After a 5-minute air dry, 62.5 ng of trypsin was added, plates were heat sealed and incubated overnight at RT. Peptides were manually extracted from the gel plugs and spotted onto MALDI target plates using the 96-tip CyBi-Well robot (CyBio, Woburn, Mass.). A fraction of the sample volumes were deposited onto a 384-format Bruker 600 µm Anchor Chip MALDI target followed by α-cyano-4-hydroxycinnamic acid matrix. Samples plus matrix were allowed to dry, followed by a wash with 1% TFA. The remainder of the samples were prepped for LC-MS/MS analysis using a Packard Multiprobe II EX liquid handling system (Perkin Elmer, Boston, Mass.). Remaining sample was transferred to narrow 96 well MTPs (220 µl), fresh extraction solution was added to the gel plugs for 30 min and the supernatant was transferred to the narrow 96 well MTP, leaving a final volume of 10 µl.

MALDI-TOF Analysis

MALDI targets were automatically run on a Bruker Biflex or Autoflex mass spectrometers. Both instrument models were equipped with delayed ion extraction, pulsed nitrogen lasers (10 Hz Biflex, 20 Hz Autoflex), dual microchannel plates and 2 GHz transient digitizers. All mass spectra represent signal averaging of 120 laser shots. The performance of the mass spectrometers produced sufficient mass resolution to produce isotopic multiplets for each ion species below m/z 3000. Spectra were internally calibrated using two spiked peptides (angiotensin II and $ACTH_{18-39}$) and database searched with a mass tolerance of 50 ppm.

LC-MS/MS Analysis

Samples that did not get positive identifications by MALDI were subjected to LC-MS/MS analysis using a LCQ mass spectrometer. A proprietary microelectrospray interface similar to an interface described previously was employed. (see Gatlin C L, Kleemann G R, Hays L G, Link A J, Yates J R, 3rd. Protein identification at the low femtomole level from silver-stained gels using a new fritless electrospray interface for liquid chromatography-microspray and nanospray mass spectrometry. *Anal Biochem* 1998; 263: 93-101; which is incorporated herein by reference). Briefly, the interface utilizes a PEEK micro-tee (Upchurch Scientific, Oak Harbor, Wash.) into which one stem of the tee is inserted a 0.025" platinum-iridium wire (Surepure Chemetals, Florham Park, N.J.) to supply the electrical connection. Spray voltage was 1.8 kV. A 15 µm i.d. PicoTip spray needle (New Objectives, Cambridge, Mass.) is inserted into another stem of the tee and aligned with the MS orifice. A 10 cm microcapillary column packed with 5 µm reversed phase C18 Zorbax material was plumbed into the last tee. A 20 µl/min flow from a Microtech UltraPlus II 3-pump solvent delivery system (Microtech Scientific, Vista, Calif.) was reduced using a splitting tee to achieve a column flow rate of ~400 nl/min Samples were injected from an Endurance autosampler (Spark-Holland, The Netherlands) onto a trapping cartridge (CapTrap, Michrom BioResources, Auburn, Calif.) with pump C. Seven minute reversed phase gradients from pumps A and B eluted peptides off the trap and capillary-LC column and into the MS. Spectra were acquired in automated MS/MS mode with a relative collision energy (RCE) preset to 35%. To maximize data acquisition efficiency, the additional parameters of dynamic exclusion, isotopic exclusion and "top 3 ions" were incorporated into the auto-MS/MS procedure. The scan range for MS mode was set at m/z 375-1400. A parent ion default charge state of +2 was used to calculate the scan range for acquiring tandem MS.

MS Data Analysis

MS data was automatically registered, analyzed and searched with the appropriate public protein/genome databases using RADARS, a separate relational database provided by Proteometrics (acquired by Harvard Biosciences, Holliston, Mass.) and optimized in-house. For MALDI peptide mapping, Mascot (Matrix Science, London, UK) and Profound (Harvard Biosciences) search engines were employed. Identifications are noted when search results are above the 95th percentile of significance in both Profound and Mascot. Mascot is used for peptide sequence searching of LC-MS/MS data. Scores above the 95th percentile are noted.

Identification of Discriminating Proteins

Identification of a relatively small number of proteins that have the ability to distinguish between different tumor types is a great challenge that is inherent in all large-scale biological assays. In order to avoid the possibility of selecting a large list of proteins for the classifier where many or all of the highly significant proteins distinguish two or only a few tumor types the follow approach was used. A series of six Wilcoxon Rank-Sum tests were performed comparing a single tumor type vs. the five remaining tumor types. This resulted in six lists of proteins that were subsequently sorted by p-value. To construct a classifier with n number of proteins the inventors simply chose the top rated protein from each of the six lists, then continued to the number 2 rated protein from each list. This process was repeated until n proteins were chosen. This general method was performed to choose any number of proteins that were needed in classifier construction.

Artificial Neural Network Construction

In order to understand the influence of different artificial neural network (ANN) architectures, the inventors constructed an automated script that allowed us to easily create a series of ANN architectures based on user supplied input parameters. For this work, the inventors chose to start with 60 input nodes and sequentially increase the number of input nodes by 30 until 600 input nodes were reached. This range was chosen for two reasons. One was to limit the number of input nodes at the beginning to a relative few so that the affect of the most useful proteins would not be overly influenced by the noise of any proteins that were included by random chance. The upper boundary was established to allow for a large number of proteins to be used in the classifier in the event that a large number of proteins contributed a relatively small amount to the overall ability of the classifier to accurately select the correct class. In addition, the problem of choosing the "right" number of hidden nodes for an ANN is intractable. Therefore, to determine the effect of the number of input nodes on classification accuracy, the inventors evaluated three different formulas for calculation of the number of hidden nodes. The formula simply divides the number of input nodes by a given value (5, 10, or 20) to determine the number of hidden nodes used in the ANN construction.

Leave One Out Cross Validation

Due to the limited number of samples in this study, the inventors used Leave One Out Cross Validation to access the accuracy of any constructed classifiers. LOOCV in some cases can be slightly optimistic and an independent training set will be needed for any further validation. It should be noted however that the inventors performed a "complete" analysis for each sample, meaning that both the gene selection procedure and subsequent ANN training steps were performed for each fold.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of determining the site of origin, within a subject, of a metastatic adenocarcinoma, comprising:
providing a protein expression profile of a plurality of metastatic adenocarcinoma types, wherein the protein expression profile comprises at least information on the isoelectric point and molecular mass;
obtaining a sample of a metastatic neoplasm from the subject;
establishing a protein expression profile for the sample, wherein the protein expression profile includes information on the isoelectric point and molecular mass; and
comparing the protein expression profile for the sample to the protein expression profile of the plurality of metastatic adenocarcinoma types, wherein the correlation between the protein expression profile for the sample and the protein expression profile of the plurality of adenocarcinomas is indicative of the site of origin of the adenocarcinoma.

2. The method of claim 1 wherein the neoplasm is selected from the group consisting of metastatic adenocarcinomas and adenomas.

3. The method of claim 1 wherein the plurality of adenocarcinomas has a site of origin selected from the group consisting of ovary, colon, kidney, breast, lung and stomach.

4. The method of claim 1 wherein the protein expression profile for the sample is compared to the protein expression profile of the plurality of adenocarcinomas using an artificial neural network.

5. The method of claim 4 wherein the protein expression profile for the sample is compared to the protein expression profile of the plurality of adenocarcinomas using a leave-one-out cross validation algorithm.

6. A method of determining the site of origin, within a subject, a metastatic adenocarcinoma, comprising:
providing a protein expression profile of a plurality of metastatic adenocarcinoma types, wherein the protein expression profile comprises at least information on the isoelectric point and molecular mass, and wherein the protein expression profile contains at least one biomarker indicative of the site of origin for an adenocarcinoma;
obtaining a sample of the adenocarcinoma from the subject;
establishing a protein expression profile for the sample;
comparing the protein expression profile for the sample to the protein expression profile of the plurality of adenocarcinomas; and
detecting the presence of the at least one biomarker in the protein expression profile for the sample, wherein the presence of the at least one biomarker is indicative of the site of origin of the adenocarcinoma.

7. The method of claim 6 wherein the plurality of metastatic adenocarcinoma types has a site of origin selected from the group consisting of ovary, colon, kidney, breast, lung and stomach.

8. The method of claim 6 wherein the biomarker of a neoplasm having a site of origin in the colon is a protein selected from the group consisting of Enoyl-CoA hydratase, mitochondrial precursor (EC 4.2.1.17) (Enoyl-CoA hydratase 1), Chloride intracellular channel protein 1 (Nuclear chloride ion channel 27) (NCC27), Myosin regulatory light chain 2, smooth muscle isoform (Myosin RLC) (LC20), Inorganic pyrophosphatase (EC 3.6.1.1) (Pyrophosphate phospho-hydrolase) (PPase), 14-3-3 protein zeta/delta (Protein kinase C inhibitor protein-1) (KCIP-1) (FAS), and Coatomer beta subunit (Beta-coat protein) (Beta-COP).

9. The method of claim 6 wherein the biomarker of a neoplasm having a site of origin in the breast is a protein selected from the group consisting of Collagen alpha 1(VI) chain precursor, Collagen alpha 1(VI) chain precursor, Aldehyde dehydrogenase, mitochondrial precursor (EC 1.2.1.3) (ALDH class 2) (ALDHI), 150 kDa oxygen-regulated protein precursor (Orp150) (Hypoxia up-regulated 1), 150 kDa oxygen-regulated protein precursor (Orp150) (Hypoxia up-regulated 1), 150 kDa oxygen-regulated protein precursor (Orp150) (Hypoxia up-regulated 1), Annexin A4 (Annexin IV) (Lipocortin IV) (Endonexin I) (Chromobindin 4) (Protein II), Glutathione S-transferase P (EC 2.5.1.18) (GST class-pi) (GSTP1-1), Collagen alpha 1(VI) chain precursor, Annexin III (Lipocortin III) (Placental anticoagulant protein III) (PAP-III), Major vault protein (MVP) (Lung resistance-related protein), WD-repeat protein 1 (Actin interacting protein 1) (AIP1) (NORI-1), Ornithine aminotransferase, mitochondrial precursor (EC 2.6.1.13), Collagen alpha 2(VI) chain precursor, Eukaryotic translation initiation factor 3 subunit 2 (eIF-3 beta) (eIF3 p36) (eIF31) (TRIP-1), Monoamine-sulfating phenol sulfotransferase (EC 2.8.2.1) (TL-PST) (HAST3), 150 kDa oxygen-regulated protein precursor (Orp150) (Hypoxia up-regulated 1), NADH-ubiquinone oxidoreductase 49 kDa subunit, mitochondrial precursor (EC 1.6.5.3), Transitional endoplasmic reticulum ATPase (TER ATPase) (15S Mg(2+)-ATPase p97 subunit), Apolipoprotein A-IV precursor (Apo-AIV), UNR-interacting protein (WD-40 repeat protein PT-WD) (MAP activator with WD repeats), and Platelet-activating factor acetylhydrolase IB gamma subunit (EC 3.1.1.47) gamma subunit).

10. The method of claim 6 wherein the biomarker of a neoplasm having a site of origin in the kidney is a protein selected from the group consisting of Major vault protein (MVP) (Lung resistance-related protein), Keratin, type I cytoskeletal 19 (Cytokeratin 19) (K19) (CK 19), Keratin, type I cytoskeletal 19 (Cytokeratin 19) (K19) (CK 19), Annexin V (Lipocortin V) (Endonexin II) (Calphobindin I) (CBP-I) (PAP-I) (PP4), Protein disulfide isomerase A3 precursor (EC 5.3.4.1) (Disulfide isomerase ER-60), Aldehyde dehydrogenase 1A1 (EC 1.2.1.3) (Aldehyde dehydrogenase, cytosolic), 14-3-3 protein sigma (Stratifin) (Epithelial cell marker protein 1), Heat shock 27 kDa protein (HSP 27) (Stress-responsive protein 27) (SRP27), 3-mercaptopyruvate sulfurtransferase (EC 2.8.1.2) (MST), Triosephosphate isomerase (EC 5.3.1.1) (TIM), Procollagen-lysine, 2-oxoglutarate 5-dioxygenase 3 precursor (EC 1.14.11.4), Stathmin (Phosphoprotein p19) (pp 19) (Oncoprotein 18) (Op18) (Metablastin), Aldehyde dehydrogenase 1A1 (EC 1.2.1.3) (Aldehyde dehydrogenase, cytosolic), Superoxide dismutase [Mn], mitochondrial precursor (EC 1.15.1.1), Alpha enolase (EC 4.2.1.11) (2-phospho-D-glycerate hydro-lyase) (Non-neural enolase), Aldehyde dehydrogenase X, mitochondrial precursor (EC 1.2.1.3) (ALDH class 2), Aspartate aminotransferase, cytoplasmic (EC 2.6.1.1) (Transaminase A), Phosphoglycerate mutase 1 (EC 5.4.2.1) (EC 5.4.2.4) (EC 3.1.3.13) (PGAM-B), Proteasome subunit alpha type 6 (EC 3.4.25.1) (Proteasome iota chain), Heteroproteinous nuclear ribonucleoproteins C1/C2 (hnRNP C1/hnRNP C2), Tubulin-specific chaperone A (Tubulin-folding cofactor A) (CFA), Aldehyde dehydrogenase X, mitochondrial precursor (EC 1.2.1.3) (ALDH class 2), Gamma enolase (EC 4.2.1.11) (2-phospho-D-glycerate hydro-lyase) (Neural enolase), Aldehyde dehydrogenase 1A1 (EC 1.2.1.3) (Aldehyde dehydrogenase, cytosolic) and Tubulin alpha-1 chain (Alpha-tubulin 1).

11. The method of claim 6 wherein the biomarker of a neoplasm having a site of origin in the lung is a protein selected from the group consisting of 78 kDa glucose-regulated protein precursor (GRP 78), Protein disulfide isomerase precursor (PDI) (EC 5.3.4.1) (P55), Calnexin precursor (Major histocompatibility complex class I antigen-binding protein p88), Macrophage capping protein (Actin-regulatory protein CAP-G), Cathepsin D precursor (EC 3.4.23.5), Thymidine phosphorylase precursor (EC 2.4.2.4) (TdRPase) (TP) (PD-ECGF) (Gliostatin), Rho GDP-dissociation inhibitor 2 (Rho GDI 2) (Rho-GDI beta) (Ly-GDI), 60 kDa heat shock protein, mitochondrial precursor (Hsp60) (60 kDa chaperonin) (CPN60), Endoplasmic reticulum protein ERp29 precursor (ERp31) (ERp28), Protein disulfide isomerase A3 precursor (EC 5.3.4.1) (Disulfide isomerase ER-60) (ERp60), Keratin, type II cytoskeletal 7 (Cytokeratin 7) (K7) (CK 7) (Sarcolectin), Elongation factor 1-delta (EF-1-delta) (Antigen NY-CO-4), Fibrinogen beta chain precursor [Contains: Fibrinopeptide B], Actin, cytoplasmic 2 (Gamma-actin), Eukaryotic translation initiation factor 3 subunit 5 (eIF-3 epsilon) (eIF3 p47 subunit), Alpha enolase (EC 4.2.1.11) (2-phospho-D-glycerate hydro-lyase) (Non-neural enolase), 2-oxoglutarate dehydrogenase E1 component, mitochondrial precursor (EC 1.2.4.2) and Tryptophanyl-tRNA synthetase (EC 6.1.1.2) (Tryptophan—tRNA ligase) (TrpRS) (IFP53).

12. The method of claim 6 wherein the biomarker of a neoplasm having a site of origin in the ovary is a protein selected from the group consisting of Lamin B1, Pyruvate dehydrogenase E1 component beta subunit, mitochondrial precursor (EC 1.2.4.1), Chloride intracellular channel protein 1 (Nuclear chloride ion channel 27) (NCC27), Rho GDP-dissociation inhibitor 1 (Rho GDI 1) (Rho-GDI alpha), Mitochondrial intermediate peptidase, mitochondrial precursor (EC 3.4.24.59) (MIP), Prohibitin, Serum albumin precursor, Calgranulin B (Migration inhibitory factor-related protein 14) (MRP-14) (P14)), Cytosol aminopeptidase (EC 3.4.11.1) (Leucine aminopeptidase) (LAP), and Tropomyosin 1 alpha chain (Alpha-tropomyosin).

13. The method of claim 6 wherein the biomarker of a neoplasm having a site of origin in the stomach is a protein selected from the group consisting of Serotransferrin precursor (Transferrin) (Siderophilin) (Beta-1-metal binding globulin), Actin-like protein 3 (Actin-related protein 3) (Actin-2), Vimentin, Phosphoglycerate mutase 1 (EC 5.4.2.1) (EC 5.4.2.4) (EC 3.1.3.13) (PGAM-B), Lamin A/C (70 kDa lamin), Selenium-binding protein 1, 14-3-3 protein zeta/delta (Protein kinase C inhibitor protein-1) (KCIP-1) (FAS), Esterase D (EC 3.1.1.1), Heteroproteinous nuclear ribonucleoprotein K (hnRNP K) (DC-stretch binding protein) (CSBP) and SM_HUMA, Endoplasmin precursor (94 kDa glucose-regulated protein) (GRP94) (gp96 homolog).

14. The method of claim 1 wherein the protein expression profile further includes information on the protein expression level.

15. The method of claim 1, wherein the protein profiles are identified using global proteomic analysis by the steps further comprising
running proteins from the plurality of metastatic adenocarcinomas on a gel;
selecting protein spots on the gel;
determining the coefficient of variation for the cell;
analyzing the protemic data using at least one Wilcoxon Rank-Sum tests; and
selecting the top rated proteins.

* * * * *

UNITED STATES PATENT AND TRADEMARK OFFICE
CERTIFICATE OF CORRECTION

PATENT NO. : 8,642,349 B1
APPLICATION NO. : 11/837883
DATED : February 4, 2014
INVENTOR(S) : Timothy J. Yeatman et al.

Page 1 of 1

It is certified that error appears in the above-identified patent and that said Letters Patent is hereby corrected as shown below:

In the Specification

Column 1, lines 11-15, should read:

GOVERNMENT SUPPORT

This invention was made with Government support under Grant No. U01CA85052 awarded by the National Institutes of Health. The Government has certain rights in the invention.

Signed and Sealed this
Second Day of June, 2015

Michelle K. Lee
*Director of the United States Patent and Trademark Office*